United States Patent [19]

Gunnell et al.

[11] Patent Number: 5,435,206
[45] Date of Patent: Jul. 25, 1995

[54] METHOD OF TESTING WELDING FILLER MATERIALS

[75] Inventors: Lyle P. Gunnell, Hartland; Duong Van Le, Milwaukee, both of Wis.

[73] Assignee: Harnischfeger Corporation, Brookfield, Wis.

[21] Appl. No.: 105,412

[22] Filed: Aug. 12, 1993

[51] Int. Cl.⁶ .............................................. B23Q 17/00
[52] U.S. Cl. ....................................... 73/866; 228/103
[58] Field of Search ........................ 73/806, 799, 850; 374/5; 228/103, 104, 105, 56.5

[56] References Cited

U.S. PATENT DOCUMENTS 3,526,948 9/1970 Stern et al. ............................ 228/103

Primary Examiner—Robert Raevis
Attorney, Agent, or Firm—Michael, Best & Friedrich

[57] ABSTRACT

A method of testing a filler material to be used in an arc welding process, the method comprising the steps of providing first and second test plates, the first test plate having a generally planar surface, and the second test plate having opposed, parallel, generally planar surfaces and a beveled edge forming a generally planar beveled surface extending at an angle from one of the opposed surfaces and forming a generally planar land which extends between the beveled surface and the other of the opposed surfaces and which extends generally perpendicular to the opposed surfaces, placing the land in abutment with the first plate surface, providing a restraining fillet weld at the junction of the other surface of the second plate and the first plate surface, and using the filler material to provide a test fillet weld at the junction of the beveled surface and the first plate surface.

10 Claims, 1 Drawing Sheet

METHOD OF TESTING WELDING FILLER MATERIALS

BACKGROUND OF THE INVENTION

The invention relates to welding, and more particularly to arc welding. Still more particularly, the invention relates to methods of testing filler materials used in arc welding.

It is known to test filler material by creating a fillet weld and then subjecting the weld joint to various tests, such as the G-BOP test, the H-Slit test and the High Restraint test. These tests are known in the art and will not be described in detail.

A prior art method of testing filler material is partially illustrated in FIG. 1. Two steel plates 10 and 14 are secured relative to each other. The plate 14 has a beveled surface 18 forming a land 22 which abuts the plate 10. A plurality of gussets 26 welded to the plates 10 and 14 secure the plates relative to each other and provide a high restraint joint between the plates. The filler material to be tested is then used in an arc welding process to form a fillet 30 between the beveled surface 18 and the plate 10. The weld joint is then subjected to the G-BOP, H-Slit and High Restraint tests. This prior art method is both expensive and time consuming. Furthermore, the absence of a visible crack in the fillet does not ensure passage of the other tests. It is therefore important that the other tests be performed.

SUMMARY OF THE INVENTION

The invention provides an improved method of testing a filler material. In the improved test, the high restraint joint of the prior art method is replaced by a medium restraint joint. This presents a much more difficult test that is consequently a much better indication of the acceptability of the filler material. In fact, to the inventors' knowledge, no filler material that has passed this improved test has subsequently failed any of the other commonly employed tests. Several filler materials have passed this improved test. The improved test is particularly suited for testing filler materials used in gas metal arc welding (GMAW), submerged arc welding (SAW) and flux core arc welding (FCAW).

More particularly, the test plates are secured relative to each other by a fillet weld rather than with gussets. The fillet weld is formed in three passes to provide, for test plates two inches thick, a fillet (hereinafter the "restraining fillet") at least one-half inch wide. The filler material is then used as in the prior art test to form a fillet between the beveled surface and the other plate. Because the joint formed by the restraining fillet is not a high restraint joint like the joint formed by the prior art gussets, the filler material is more likely to crack upon solidification. It is therefore easier for a filler material to fail this test than the prior art test. Conversely, a filler material that passes this test is more likely (and apparently certain) to pass the other known tests. This test is also less expensive and less time consuming than the prior art test.

Other features and advantages of the invention will become apparent to those skilled in the art upon review of the following detailed description, claims and drawings.

Figure 1:
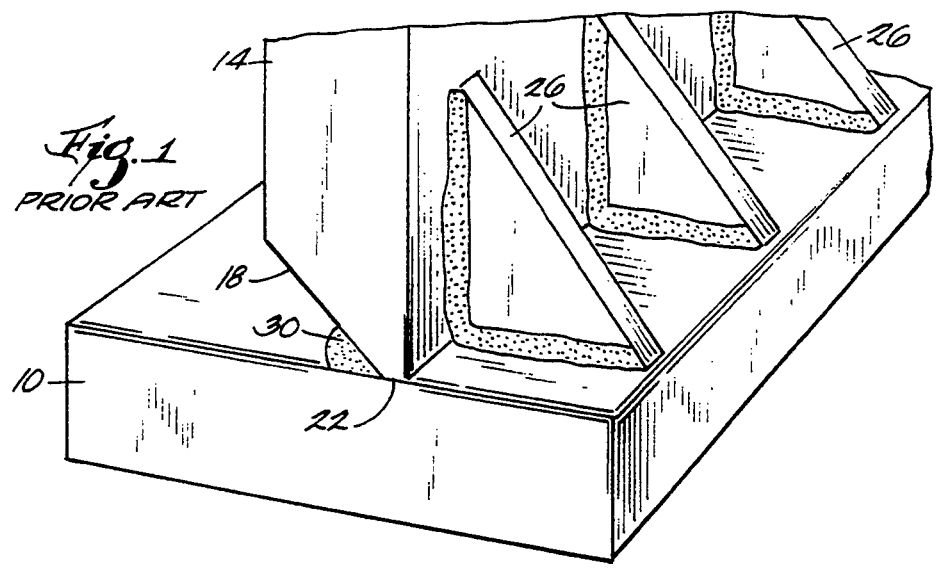
FIG. 1 is a perspective view of a weld joint used in a prior art filler material test.

Before one embodiment of the invention is explained in detail, it is to be understood that the invention is not limited in its application to the details of the construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DESCRIPTION OF THE PREFERRED EMBODIMENT

Figure 2:
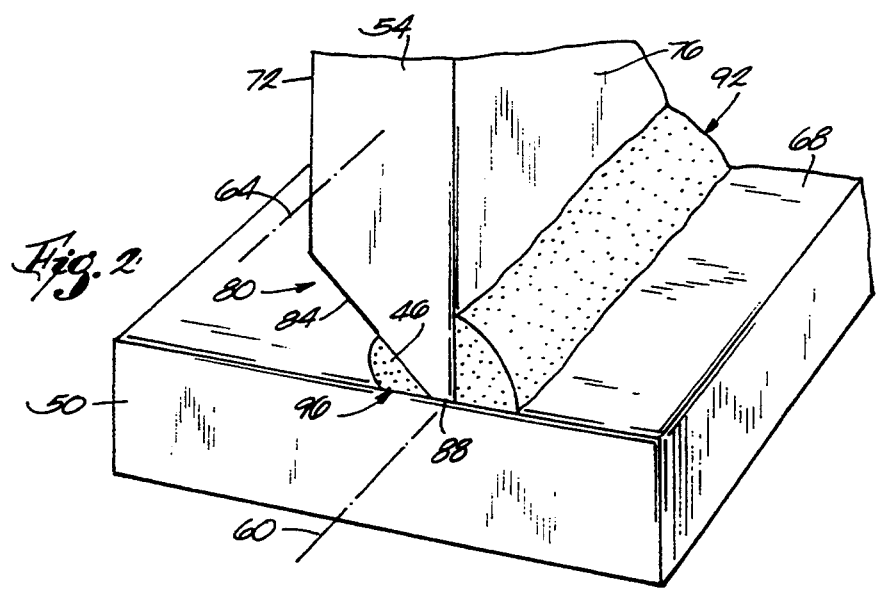
FIG. 2 is a view similar to FIG. 1 showing a weld joint used in a filler material test in accordance with the invention.
Figure 3:
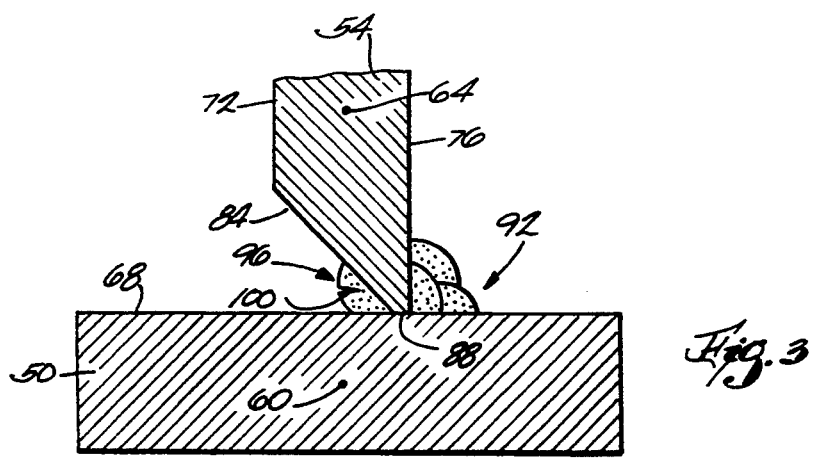
FIG. 3 is a cross-sectional view of the weld joint shown in FIG. 2 and showing a crack in the filler material.

A method of nesting a filler material 46 in accordance with the invention is illustrated in FIGS. 2 and 3.

Test plates 50 and 54 are secured together as described below. The plates 50 and 54 have respective longitudinal axes 60 and 64. The plates 50 and 54 are preferably made of steel, specifically A633 or A514 steel. Although the plates 50 and 54 could have various dimensions, the illustrated plates are twenty inches long, six inches wide and two inches thick. The plate 50 has a planar surface 68. The plate 54 has opposed, parallel, planar surfaces 72 and 76. The plate 54 also has a beveled edge 80 forming a planar beveled surface 84 extending at an angle of approximately 45 degrees from the surface 72 and forming a planar land 88 which extends between the beveled surface 84 and the surface 76 and which extends perpendicular to the surfaces 72 and 76. The land 88 is preferably one-quarter inch thick.

The land 88 is placed in abutment with the plate surface 68, with the longitudinal axes 60 and 64 parallel, and the plates 50 and 54 are arc welded together to provide a restraining fillet weld 92 at the junction of the surfaces 68 and 76. The weld 92 is preferably formed in three passes, as illustrated in FIG. 3. The weld 92 forms a medium restraint joint between the plates 50 and 54.

Next, the surfaces 68 and 84 are arc welded using the filler material 46 being tested. In other words, the filler material 46 is used to provide a test fillet weld 96 at the junction of the surfaces 68 and 84. The test weld 96 is formed in a single pass.

Next, the welded plates 50 and 54 are cut generally perpendicular to the longitudinal axes 60 and 64 of the plates 50 and 54 so that the test weld 96 can be examined. Visual examination of the weld 96 is sufficient. The filler material 46 is unacceptable if any cracks are visible in the filler material. A crack 100 is illustrated in FIG. 3.

As stated previously, this test is relatively inexpensive and takes relatively little time. Additionally, to the inventors' knowledge, no filler material that has passed this test has subsequently failed other commonly employed tests. The test is particularly suited for testing filler materials used in gas metal arc welding (GMAW), submerged arc welding (SAW) and flux core arc welding (FCAW).

Assuming no cracks are visible in the weld 96, the weld can then be subjected to G-Bop, H-Slit and High Restraint tests.

Various features of the invention are set forth in the following claims.

We claim:

1. A method of testing a filler material to be used in an arc welding process, said method comprising the steps of providing first and second test plates, said first test plate having a generally planar surface, and said second test plate having opposed, parallel, generally planar surfaces and a beveled edge forming a generally planar beveled surface extending at an angle from one of said opposed surfaces and forming a generally planar land which extends between said beveled surface and the other of said opposed surfaces and which extends generally perpendicular to said opposed surfaces, placing said land in abutment with said first plate surface, providing a restraining fillet weld at the junction of said other surface of said second plate and said first plate surface so that said other surface and said first plate surface are secured to each other solely by said restraining fillet weld and without gussets, and using said filler material to provide a test fillet weld at the junction of said beveled surface and said first plate surface.

2. A method as set forth in claim 1 wherein said restraining weld is formed in three passes.

3. A method as set forth in claim 1 wherein said test weld is formed in a single pass.

4. A method as set forth in claim 1 wherein said beveled surface extends at an angle of approximately forty-five degrees from said one of said opposed surfaces.

5. A method as set forth in claim 1 wherein said restraining weld forms a medium restraint joint between said plates.

6. A method as set forth in claim 1 and further comprising the step of examining said test weld for cracks.

7. A method as set forth in claim 1 wherein said test weld is formed by one of gas metal arc welding, flux core arc welding, and submerged arc welding.

8. A method as set forth in claim 1 wherein said restraining fillet weld extends along substantially the entire length of said junction of said other surface and said first plate surface.

9. A method of testing a filler material to be used in an arc welding process, said method comprising the steps of providing first and second test plates, said first test plate having a generally planar surface, and said second test plate having opposed, parallel, generally planar surfaces and a beveled edge forming a generally planar beveled surface extending at an angle of approximately forty-five degrees from one of said opposed surfaces and forming a generally planar land which extends between said beveled surface and the other of said opposed surfaces and which extends generally perpendicular to said opposed surfaces, placing said land in abutment with said first plate surface, forming in three passes a restraining fillet weld at the junction of said other surface of said second plate and said first plate surface so as to provide a medium restraint joint between said plates, said restraining fillet weld extending along substantially the entire length of said junction of said other surface and said first plate surface so that said other surface and said first plate surface are secured to each other solely by said restraining fillet weld and without gussets, using said filler material to form in one pass a test fillet weld at the junction of said beveled surface and said first plate surface, and examining said test weld for cracks.

10. A method as set forth in claim 9 wherein said test weld is formed by one of gas metal arc welding, flux core arc welding, and submerged arc welding.

* * * * *

UNITED STATES PATENT AND TRADEMARK OFFICE
CERTIFICATE OF CORRECTION

PATENT NO. : 5,435,206
DATED      : July 25, 1995
INVENTOR(S): Lyle P. Gunnell and Duong Van Le It is certified that error appears in the above-identified patent and that said Letters Patent is hereby corrected as shown below:

Column 2, line 25, delete "nesting" insert -- testing --

Signed and Sealed this

Nineteenth Day of September, 1995

Attest:

BRUCE LEHMAN

*Attesting Officer*    *Commissioner of Patents and Trademarks*